(12) United States Patent
Vishnupad

(10) Patent No.: US 6,462,025 B2
(45) Date of Patent: Oct. 8, 2002

(54) ANTIBIOTIC/BENZOYL PEROXIDE DISPENSER

(75) Inventor: Mohan Vishnupad, Easton, CT (US)

(73) Assignee: Imaginative Research Associates, Inc., Milford, CT (US)

( * ) Notice: Subject to any disclaimer, the term of this patent is extended or adjusted under 35 U.S.C. 154(b) by 0 days.

(21) Appl. No.: 09/734,748

(22) Filed: Dec. 12, 2000

(65) Prior Publication Data

US 2002/0110594 A1 Aug. 15, 2002

(51) Int. Cl.[7] .......................... A61K 31/70; A61K 31/74
(52) U.S. Cl. .................... 514/29; 424/78.02; 424/78.03; 514/24; 514/152; 514/154; 514/714; 514/859
(58) Field of Search ........................... 514/29, 24, 152, 514/154, 714, 859; 424/78.02, 78.03

(56) References Cited

U.S. PATENT DOCUMENTS

| | | |
|---|---|---|
| 3,535,422 A | 10/1970 | Cox et al. |
| 3,969,516 A | 7/1976 | Stoughton |
| 4,000,263 A | 12/1976 | Hebborn |
| 4,056,615 A | 11/1977 | Vora et al. |
| 4,075,333 A | 2/1978 | Josse |
| 4,124,707 A | 11/1978 | Green et al. |
| 4,387,107 A | 6/1983 | Klein et al. |
| 4,388,301 A | 6/1983 | Klein |
| 4,469,684 A | 9/1984 | Huggins et al. |
| 4,497,794 A | 2/1985 | Klein et al. |
| 4,532,133 A | 7/1985 | Schmidt |
| 4,599,379 A | 7/1986 | Flesher et al. |
| 4,628,078 A | 12/1986 | Glover et al. |
| 4,692,329 A | 9/1987 | Klein et al. |
| 4,826,048 A | 5/1989 | Skorka et al. |
| 4,840,970 A | 6/1989 | Ohasi et al. |
| 4,888,363 A | 12/1989 | Dulak et al. |
| 4,963,348 A | 10/1990 | Bolich, Jr. et al. |
| 4,966,779 A | 10/1990 | Kirk |
| 5,004,598 A | 4/1991 | Lochhead et al. |
| 5,185,372 A | 2/1993 | Ushio et al. |
| 5,242,433 A | 9/1993 | Smith et al. |
| 5,296,505 A | 3/1994 | Solladie et al. |
| 5,356,040 A | 10/1994 | Reggiani |
| 5,417,674 A | 5/1995 | Smith et al. |
| 5,446,028 A | 8/1995 | Klein et al. |
| 5,460,620 A | 10/1995 | Smith et al. |
| 5,470,323 A | 11/1995 | Smith et al. |
| 5,562,642 A | 10/1996 | Smith et al. |
| 5,632,996 A | 5/1997 | Ramirez et al. |
| 5,767,098 A | 6/1998 | Klein et al. |
| 5,823,391 A | 10/1998 | Klauke et al. |
| 6,013,637 A | 1/2000 | Klein et al. |
| 6,020,367 A | 2/2000 | Duffy et al. |

OTHER PUBLICATIONS

BF Goodrich, Carbopol Resins (Nov. 1990).
SEPPIC, SEPIGEL *305 (Mar. 1995).
BF Goodrich Specialty Chemicals, Carbopol ETD 2020, For Personal Care Applications (Sep. 1993).
BF Goodrich Specialty Chemicals Dilip D. Desai, et al Carbopol Ultrez 10 Polymer; A New Universal Thickener for the Personal Care Industry (Aug. 1995).
BF Goodrich Specialty Chemicals, Carbopol High Performance Polymers for Personal Care, Optimizing Surfactant Systems Thickened with Carbopol ETD 2020 Polymer Using a Statistical Design (Mar. 1995).
BF Goodrich Specialty Chemicals, Carbopol ETD Resins: Formulation Tips, Carbopol High Performance Polymers, TDS–207 (Mar. 1995).
BF Goodrich Specialty Chemicals, Carbopol Ultrez Polymer, Carbopol Ultrez 10 Polymer for Personal Care Applications (Mar. 1995).

*Primary Examiner*—Elli Peselev
(74) *Attorney, Agent, or Firm*—Carter, DeLuca, Farrell & Schmidt, LLP

(57) ABSTRACT

Two separate compositions, one containing an antibiotic and one containing benzoyl peroxide are packaged within and dispensed from a common dispenser. More particularly, a dual dispenser contains i) a first composition that is substantially anhydrous and includes a polar solvent, an antibiotic and a thickening agent selected from the group consisting of acrylic acid polymers and polyacrylamides; and ii) a second composition containing benzoyl peroxide or, alternatively, a retinoid. By packaging these two anti-acne active ingredients in this manner, long shelflife and convenient dispensing and application are provided.

24 Claims, 1 Drawing Sheet

ANTIBIOTIC/BENZOYL PEROXIDE DISPENSER

BACKGROUND

1. Technical Field

This disclosure relates to compositions and apparatus for dispensing two distinct substances. More specifically, this disclosure relates to compositions and apparatus which allow long-term storage and subsequent dispensing of two compositions, to wit, a first composition containing an antibiotic (such as erythromycin or clindamycin) and a second composition containing benzoyl peroxide or, alternatively, a retinoid.

2. Background of Related Art

Acne is a common inflammatory disease of human skin, and concentrates in skin areas where sebaceous glands are largest, most numerous, and most active. In its milder types, it is a more or less superficial disorder which is evidenced by slight, spotty irritations and ordinary skin hygiene is a satisfactory treatment. However, in the more inflammatory types of acne, bacterial invasion of or about the pilosebaceous follicles occurs and pustules, infected cysts and, in extreme cases, canalizing inflamed and infected sacs appear. These lesions may become extensive and leave permanent, disfiguring scars.

Acne is very common by puberty and at least 80% of teenagers are afflicted. The facial eruptions are known to cause such psychic trauma in many adolescents that they find it difficult to make personal adjustments and consequently, withdraw and self-pity occur. The sufferer may be constantly aware of the obvious facial blemishes. For these reasons a medicinal preparation and treatment are of definite benefit and may eliminate the need for psychotherapy.

To reduce the severity of acne, various forms of medication have previously been topically applied to the skin. Antibacterial soaps have been used as well as bactericidal agents such as sulfur and resorcinol. Other topical compositions have separately contained benzoyl peroxide, hexachlorophene, erythromycin or neomycin sulfate. None of these prior preparations has been completely effective.

As disclosed by Klein et al. (U.S. Pat. No. 4,497,794), it was discovered that a mixture on the skin of a peroxide, especially benzoyl peroxide and an antibiotic or antibacterial such as clindamycin, neomycin, sodium sulfacetamide, sulfur, tetracycline or erythromycin is particularly beneficial as they can exert a statistically significant synergistic effect. Peroxides inhibit the formation of free fatty acids in the skin, primarily through inactivation of extracellular lipase (via oxidation) necessary to cleave triglycerides into free fatty acids and glycerol. The antibiotic or antibacterial component reduces the concentration of Corynebacterium acnes (i.e., P. acnes), a normal anaerobic bacteria which is the prime source of the lipase. Instead of the benzoyl peroxide, which is preferred, peroxides such as stabilized hydrogen peroxide and peroxides of organic acids, such as a lauroyl peroxide, may be used.

As disclosed by Klein et al., erythromycin and benzoyl peroxide may be applied to the skin in combination in a preformulated aqueous-alcoholic gel. However, if a mixture is first made up and then applied to the skin, it is best that the mixture be made at the time of application or that the mixture be used within twenty-four hours. The prompt use of a premix is necessary due to the chemical incompatibility of the two active agents. Because of this, it is advisable that the two agents be put in separate vials, bottles or other containers. For example, the Klein et al. patent discloses a kit containing, separately bottled liquid compositions comprising 5% benzoyl peroxide and a solution of erythromycin in ethanol or acetone.

However, separately packaging multiple dosages of the two active ingredients presents a number of disadvantages to the end-user. For example, a unit application dosage of each active must be removed sequentially from each container and absorbed onto an applicator, such as a cotton swab, so that it can be coated onto the skin of the user. This provides opportunities for spillage or over- or under-dosing, which can lead to skin irritation and other side effects. Furthermore, such a multidose system necessarily adds to the costs of packaging, shipping and storage.

A dispensing and applicator system intended to overcome these difficulties is disclosed in U.S. Pat. No. 5,562,642. A dual-pad package is disclosed therein that purportedly can contain, preserve and deliver single unit doses of two or more chemically- or physically-incompatible active ingredients. For example, an antibiotic in combination with a liquid, semi-liquid (cream) or gelled aqueous or non-aqueous vehicle can be absorbed by and retained by the first pad and a second ingredient which is physically- or chemically-incompatible with the antibiotic, such as a peroxide, can be absorbed and retained by the second pad, preferably in combination with the appropriate vehicle.

It would be desirable to provide a means for simultaneously dispensing two active acne treating compounds in aesthetically acceptable vehicles which allow prolonged shelf life for both active compounds and easy mixing just prior to application to the skin.

SUMMARY

It has now been discovered that two separate compositions, one containing an antibiotic and one containing benzoyl peroxide can be packaged within and dispensed from a common dispenser. More particularly, a dual dispenser contains i) a first composition that is substantially anhydrous and includes a polar solvent, an antibiotic and a thickening agent selected from the group consisting of acrylic acid polymers and polyacrylamides; and ii) a second composition containing benzoyl peroxide. Preferably, the first and second compositions have viscosities that differ by no greater than 25%. By packaging these two anti-acne active ingredients in this manner, long shelflife and convenient dispensing and application are provided.

In an alternate embodiment, two separate compositions, one containing an antibiotic and one containing a retinoid are packaged within and dispensed from a common dispenser. More particularly, a dual dispenser contains i) a first composition that is substantially anhydrous and includes a polar solvent, an antibiotic and a thickening agent selected from the group consisting of acrylic acid polymers and polyacrylamides; and ii) a second composition that is substantially anhydrous, and includes a polar solvent, a retinoid, and a thickening agent selected from the group consisting of acrylic acid polymers and polyacrylamides.

BRIEF DESCRIPTION OF THE DRAWINGS

Various embodiments are described herein with reference to the drawing wherein.

DETAILED DESCRIPTION OF PREFERRED EMBODIMENTS

Figure 1:
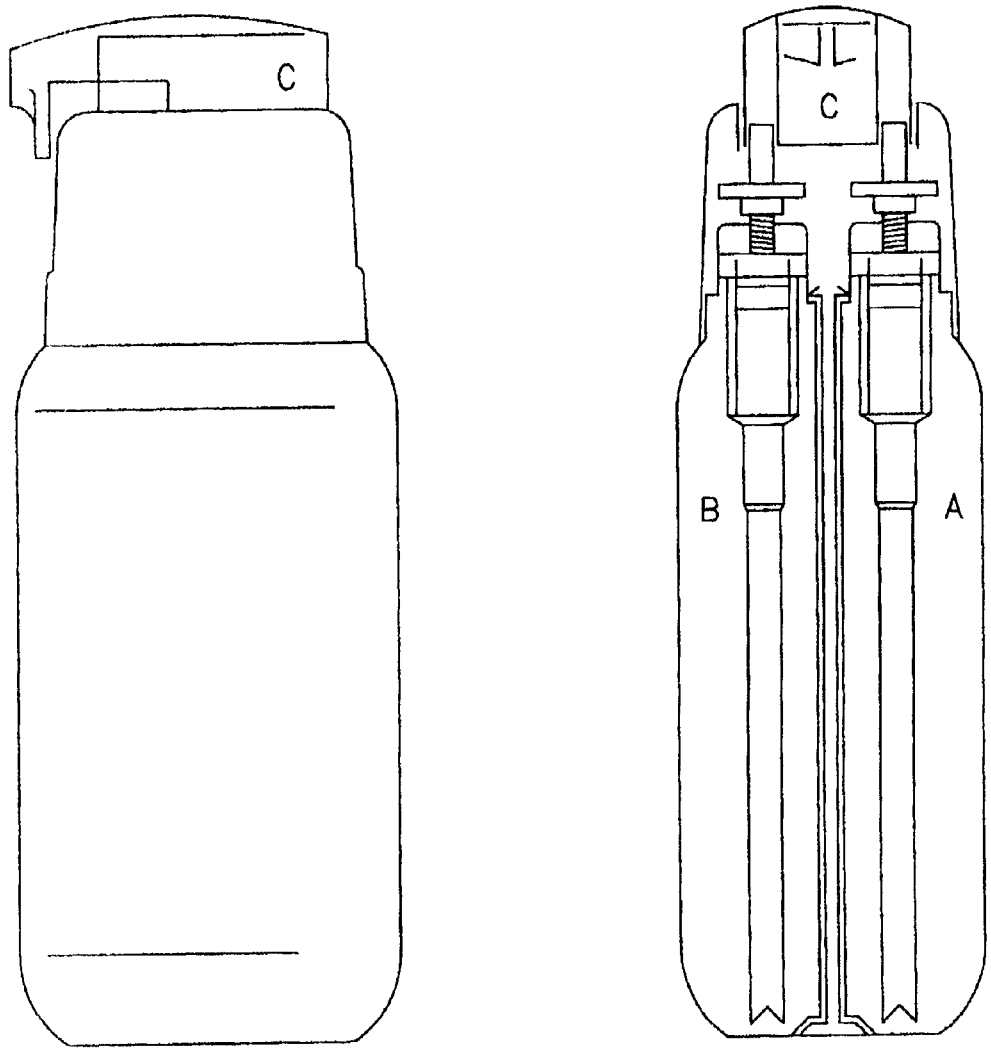
FIG. 1 is an schematic view of a container suitable for dispensing the first and second compositions in accordance with this disclosure.

Antibiotic in a first, substantially anhydrous composition is dispensed simultaneously with a second, benzoyl peroxide-containing composition in accordance with this disclosure.

By the term "substantially anhydrous" it is meant that, other than water of hydration contained in the various components used to formulate the composition, no free water is added to the composition. Typically, the water content of the composition will be less than 5% by weight. Preferably the water content of the composition is less than 3% and most preferably less than about 1% by weight of the composition.

The first composition is substantially anhydrous and contains a polar solvent, a thickening agent and an antibiotic. Preferably the antibiotic is one known to be useful in treating acne, such as, for example, erythromycin, tetracyclin, clindamycin, their derivatives or pharmaceutically acceptable salts. The antibiotic is preferably present in the first composition in an amount from about 0.001 wt. % to about 5 wt. %, more preferably about 0.1 wt. % to about 1.0 wt. %.

The first composition has a viscosity greater than about 1000 centipoise (cps) when measured using a Brookfield viscometer (model LVT) at room temperature using spindle number 3 or 4 at 0.3 to 30 rpm. It should be understood that all viscosities referred to herein are measured in this manner. Preferably, the first composition has a viscosity greater than 5,000 cps. In particularly useful embodiments, the first composition has a viscosity in the range of from about 1000 to about two million centipoise. Most preferably, the first composition has a viscosity in the range of about 10,000 cps to about 1,000,000 cps.

Polar solvents useful in the first composition include polyols. A polyol is a compound with at least two hydroxyl groups per molecule, i.e., a compound having multiple hydroxyl groups as part of its molecular structure. Among the useful polyols are polyhydric alcohols. Propylene glycol, dipropylene glycol, polyethylene glycol and glycerine are particularly preferred polar solvents for use in the first composition.

The thickening agent used in the first composition is selected from the group consisting of acrylic acid polymers and polyacrylamides. The thickening agent are used in an amount sufficient to obtain a composition of viscosity in the desired range.

Useful acrylic acid polymers include copolymers of (meth)acrylic acid and of monomers containing at least one fatty chain; these monomers are chosen from hydrophobic monomers with a fatty chain, amphiphilic monomers containing a hydrophobic part with a fatty chain and a hydrophilic part, or alternatively their mixtures. Suitable materials include, for example, copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerythritol. These copolymers are commonly referred to as acrylates/$C_{10-30}$ alkyl acrylate crosspolymers and are commercially available under the tradename CARBOPOL® from B.F. Goodrich, Cleveland, Ohio U.S.A. Other polymers useful in the preparation of the present compositions are polymers of polyacrylic acid crosslinked with from about 0.75% to about 2.0% of polyalkyl sucrose or polyalkyl pentaerythritol often with molecular weights of 4 to 5 million or more that are commercially available, for example, under the trade designation CARBOPOL® 934, 940 and 941 from B.F. Goodrich, Cleveland, Ohio U.S.A. Anionic amphiphilic polymers which comprise 95% to 60% by weight of acrylic recurring structural units, 4% to 40% by weight of acrylate recurring structural units and 0.1% to 6% by weight of crosslinking monomer, or (ii) which comprise 98% to 96% by weight of acrylic recurring structural units, 1% to 4% by weight of acrylate recurring structural units and 0.1% to 0.6% by weight of crosslinking monomer are also useful as the thickening agent in the present compositions. Such polymers include, for example, those hydrophobically-modified cross-linked polymers of acrylic acid having amphipathic properties marketed by B.F. Goodrich under the trademarks CARBOPOL® 1342 and CARBOPOL® 1382. Also useful is ULTREZ® 10 (available from B. F. Goodrich), an oil in water emulsion of a modified acrylic copolymer comprising of a major portion of a monoolefinically unsaturated carboxylic acid monomer or its anhydride having a length of from about 3 to 6 carbon atoms and a minor portion of a $C_{8-30}$ chain acrylate or methacrylate ester monomer wherein the carboxylic acid or its anhydride is from about 80 to about 99% by weight and the $C_{8-30}$ chain acrylate or methacrylate ester monomer is from about 1% to about 20% by weight. The polymer is described in U.S. Pat. No. 5,004,598, hereby incorporated by reference in its entirety.

When used, these acrylic acid polymers are present in the first composition at a level from about 0.05% to about 20%, preferably from about 0.5% to 10% and most preferably from about 1% to about 10%.

The first composition can alternatively contain polyacrylamide polymers as the thickening agent, especially non-ionic polyacrylamide polymers. The non-ionic polymers useful in the first composition are polyacrylamides and substituted polyacrylamides, branched or unbranched. These polymers are non-ionic polymers which can be formed from a variety of monomers including acrylamide and methacrylamide which are unsubstituted or substituted with one or two alkyl groups (preferably $C_{1-5}$). Preferred acrylate amides and methacrylate amides in which the amide nitrogen is unsubstituted, or substituted with one or two $C_{1-5}$ alkyl groups (preferably: methyl, ethyl or propyl), for example, acrylamide, methacrylamide, N-methylacrylamide, N-methylmethacrylamide, N,N-dimethylmethacrylamide, N-isopropylacrylamide, N-isopropylmethacrylamide and N,N-dimethylacrylamide. These monomers are generally disclosed in U.S. Pat. No. 4,963,348 which is incorporated by reference herein in its entirety. These copolymers may optionally be formed using conventional neutral crosslinking agents such as dialkenyl compounds. The use of such crosslinking agents for cationic polymers is disclosed in U.S. Pat. Nos. 4,628,078 and 4,599,379 both of which are incorporated by reference herein. These non-ionic copolymers may have a molecular weight greater than about 1,000,000 preferably greater than about 1,500,000 and range up to about 30,000,000. Most preferred among these polyacrylamide polymers is the non-ionic polymer given the CTFA designation polyacrylamide and isoparaffin and laureth-7, available under the tradename SEPIGEL® 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

When used, these non-ionic polyacrylamides are present in the first composition at a level from about 0.05% to about 20%, preferably from about 0.5% to 10% and most preferably from about 1% to about 10%.

Quite surprisingly, it has been found that contrary to product literature relating to the commercially available acrylic acid polymers and polyacrylamides, when used in the first, substantially anhydrous composition, the thickening agents need not be dispersed in an aqueous medium or neutralized to provide the desired thickening.

The second composition contains benzoyl peroxide. The second composition can be any benzoyl peroxide-containing cream, lotion, gel or suspension. Examples of benzoyl peroxide compositions that are suitable for use in accordance with this disclosure include, but are not limited to the compositions disclosed in U.S. Pat. No. 5,632,996, the disclosure of which is incorporated herein by reference. In particularly useful embodiments, the second composition is also substantially anhydrous. Among these embodiments are compositions containing a) a polar solvent, b) a thickening agent selected from the group consisting of acrylic acid polymers, polyacrylamides and combinations thereof, c) benzoyl peroxide, d) alkyl benzoate and, optionally e) a synthetic cleanser. Suitable synthetic cleansers include, but are not limited to sodium cocoyl isethionate, alpha olefin sulfonate sarcosynates and acyl glutamates.

The amount of benzoyl peroxide in the second composition can be from about 0.1 to about 20 percent by weight based on the total weight of the second composition, preferably from about 1.0 to about 15 weight percent, most preferably from about 1.5 to about 10 weight percent.

In an alternative embodiment, the second compositions is also substantially anhydrous and contains a polar solvent, a thickening agent and a retinoid. Suitable retinoids, include, for example, retinol, retinoic acid, retinyl palmitate, retinyl propionate or retinyl acetate as well as synthetic retinoid mimics. The retinoid is preferably present in the second composition in an amount from about 0.001 wt. % to about 5 wt. %, more preferably about 0.1 wt. % to about 2.0 wt. %. Suitable polar solvents and thickening agents for the second composition are the same as described above for the first composition. In this alternative embodiment, the second, retinoid-containing composition can have a viscosity greater than about 1000 centipoise (cps) when measured using a Brookfield viscometer (model LVT) at room temperature using spindle number 3 or 4 at 0.3 to 30 rpm. Preferably, the second, retinoid-containing composition has a viscosity greater than 5,000 cps. In particularly useful embodiments, the second, retinoid-containing composition has a viscosity in the range of from about 1000 to about two million centipoise. Most preferably, the second, retinoid-containing composition has a viscosity in the range of about 10,000 cps to about 1,000,000 cps.

The first and second compositions preferably have viscosities that are similar to provide a cosmetically elegant product when the first and second compositions are simultaneously dispensed. In particularly useful embodiments the difference in viscosity between the first and second compositions is no more than about 25%.

In addition to the above-listed ingredients, one or both of the first and second compositions may also contain a variety of non-essential ingredients such as, for example, co-solvents, preservatives, emollients, humectants, anti-inflammatory agents, antioxidants, insect repellents or skin cooling compounds, etc.

For example, either of the first or second composition may contain one or more co-solvents, such as ethanol, acetone or propylene carbonate.

A preservative can also be used in either or both of the first or second compositions. Preservatives suitable for use in connection with the present compositions include parabens, sorbates, benzyl alcohol, diazolidinyl urea and isothiazolinones. Preservatives can be present in an amount from about 0.001 wt. % to about 15 wt. % of the total composition.

One or both of the first or second compositions can also be formulated to contain about 0.01 wt. % to about 30 wt. %, preferably about 1.0 wt. % to about 15 wt. % of the total composition, skin cooling compounds, such as menthol, methyl glycerol, asymmetrical carbonates, thiocarbonates and urethanes, substituted carboxamides, ureas or phosphine oxides as described in J. Cosmet. Chem., vol. 29, page 185 (1978) and incorporated herein by reference, methyl lactate and menthone glycerin acetal.

The first substantially anhydrous antibiotic compositions and the second benzoyl peroxide composition are stored in and dispensed from a multi-chamber dispenser. Dispensing systems suited for simultaneously dosing two separately contained incompatible compounds, are well known. As such, the dispensing system schematically depicted in FIG. 1 (dispenser from Maplast, Tradate, Italy) is just one example out of a number of products which range from small, two-chambered single use pouches to tubes using different product compartments or tubes compartmentalized using extrudable, viscous and relatively inert materials to separate the incompatible compounds.

The dispenser shown in FIG. 1 is able to simultaneously dose two compounds separately contained in A and B by pressing dosing head C. Pressing dosing head C activates two small pumps which subsequently dispense the two compounds in approximately equal volumes. Depending on the design of the dosing head, the compounds can be dosed in two separate streams or in just one stream.

If desired, a dispensing unit that is able to deliver The first and second substantially anhydrous compositions in a ratio, such as, for example, 1:2 can be used. Translated to the dispenser depicted in FIG. 1, this would mean that one of the two pumps is able to dose at least twice the volume of the other pump in just one stroke of dosing head C. Translated to a two-chambered single use pouch, this would mean that the chamber containing the first substantially anhydrous composition contains at least half as much product volume as the other chamber. Translated to a two-compartment tube, this would mean that under equal pressure the discharge orifice for the compartment containing the first substantially anhydrous composition allows the passage of at least twice as much product as the discharge orifice of the other compartment. Translated to a tube which is compartmentalized using extrudable material, this would mean that first substantially anhydrous composition is present inside the tube in at least double the volume of the second substantially anhydrous composition.

Other suitable dispensers are disclosed in U.S. Pat. Nos. 5,356,040; 5,823,391, and 4,826,048 the disclosures of which are incorporated herein by this reference.

The following examples are presented to illustrate specific embodiments of the present compositions and methods. These examples should not be interpreted as limitations upon the scope of the invention.

EXAMPLES I–IV

The following formulations are exemplary of substantially anhydrous antibiotic compositions suitable for use as the first composition:

|  | I | II | III | IV |
|---|---|---|---|---|
| erythromycin | 2 | 2 | — | 2.0 |
| propylene glycol | 96 | 71.5 | 96.0 | 96.0 |
| ULTREZ 10 | 2 | 1.5 | 2.0 | 1.0 |
| polyethylene glycol | — | 25.0 | — | |
| clindamycin | — | — | 1.0 | |
| SEPIGEL 305 | | | | 1.0 |

EXAMPLES V–VI

The following exemplary benzoyl peroxide-containing formulations are suitable for use as the second composition to be dispensed simultaneously with any of the anhydrous formulations of Examples I–IV.

| V | |
|---|---|
| Petrotalium | 15.50 |
| Sodium Cocoyl Isethionate | 5.00 |
| Alfa olefin Sulfonate | 2.00 |
| Titaniam Dioxide | 0.30 |
| Lucidol 75% (Benzoyl Peroxide) | 15.80 |
| $C_{12-15}$ Alkyl Benzoate | 7.00 |
| Triethanolamine | 0.60 |
| Carbopol 1382 | 0.80 |
| Glycerin | 58.0 |
| VI - Gel Composition | |
| Water | 56.4 |
| Glycerine | 5.0 |
| SEPIGEL 305 | 2.0 |
| Sodium Hydroxide | 1.60 |
| Steareth S-20 | 2.0 |
| Steareth S-2 | 2.0 |
| Cetyl Stearyl Alcohol | 3.0 |
| Silicone Cupoydoyl | 5.0 |
| Lucidol 75% (Benzoyl Peroxide) | 16.0 |
| $C_{12-15}$ Benzoate Ester | 7.00 |
| VII - Benzoyl Peroxide Gel | |
| propylene glycol | 88.5 |
| ULTREZ 10 | 1.5 |
| Benzoyl Peroxide | 5.0 |
| Fin Solv TN | 5.0 |
| VIII - Benzoyl Peroxide Gel Cleanser | |
| glycerin | 66.0 |
| ULTREZ 10 | 2.0 |
| Benzoyl Peroxide | 5.0 |
| Fin Solv TN | 5.0 |
| Sodium Cocoyl Isethionate | 20.0 |

It will be understood that various modifications may be made to the embodiments disclosed herein. Therefore, the above description should not be construed as limiting, but merely as exemplifications of preferred embodiments. Those skilled in art will envision other modifications within the scope and spirit of the claims appended hereto.

We claim:

1. An apparatus comprising:
    a first chamber containing a first composition, the first composition being substantially anhydrous and comprising i) a polar solvent; ii) an antibiotic; and iii) a thickening agent in an amount sufficient to impart to the first composition a viscosity of at least 1000 cenetipoise measured at room temperature, the thickening agent being selected from the group consisting of acrylic acid polymers, polyacrylamides and combinations thereof;
    a second chamber containing a second composition comprising benzoyl peroxide; and
    one or more outlets for dispensing the first and second compositions.

2. An apparatus as in claim 1 wherein the first composition contains a thickening agent selected from the group consisting of copolymers of $C_{10\text{-}30}$ alkyl acrylates with one or more monomers of acrylic acid, methacrylic acid, or one of their short chain (i.e., $C_{1\text{-}4}$ alcohol) esters, crosslinked with an allyl ether of sucrose or pentaerythritol, polymers of polyacrylic acid crosslinked with from about 0.75% to about 2.0% of polyalkyl sucrose or polyalkyl pentaerythritol, anionic amphiphilic polymers which comprise 95% to 60% by weight of acrylic recurring structural units, 4% to 40% by weight of acrylate recurring structural units and 0.1% to 6% by weight of a crosslinking monomer, polymers which comprise 98% to 96% by weight of acrylic recurring structural units, 1% to 4% by weight of acrylate recurring structural units and 0.1% to 0.6% by weight of a crosslinking monomer, and copolymers of (meth)acrylic acid and of monomers containing at least one fatty chain, the monomers being selected from the group consisting of hydrophobic monomers with a fatty chain, amphiphilic monomers containing a hydrophobic part with a fatty chain and a hydrophilic part and mixtures thereof.

3. An apparatus as in claim 1 wherein the first composition contains a thickening agent selected from the group consisting of polyacrylamides and substituted polyacrylamides, branched or unbranched.

4. An apparatus as in claim 1 wherein the first composition contains as the thickening agent a mixture of polyacrylamide, $C_{13}$–$C_{14}$ isoparaffin and Laureth 7.

5. An apparatus as in claim 1 wherein the first composition contains a thickening agent at a level from about 0.05% to about 20% by weight of the composition.

6. An apparatus as in claim 1 wherein the first composition contains a thickening agent at a level from about 0.5% to about 10% by weight of the composition.

7. An apparatus as in claim 1 wherein the first composition contains a thickening agent at a level from about 1% to about 10% by weight of the composition.

8. An apparatus as in claim 1 wherein the first composition contains a polar solvent selected from the group consisting of polyols.

9. An apparatus as in claim 1 wherein the first composition contains a polar solvent comprising one or more compounds selected from the group consisting of polyhydric alcohols.

10. An apparatus as in claim 1 wherein the first composition contains a polar solvent comprising one or more compounds selected from the group consisting of propylene glycol, dipropylene glycol, polyethylene glycol and glycerine.

11. An apparatus as in claim 1 wherein the first composition contains an antibiotic selected from the group consisting of erythromycin, clindamycin, tetracycline, derivatives of erythromycin, clindamycin, or tetracycline and pharmaceutically acceptable salts of erythromycin, clindamycin or tetracycline.

12. An apparatus as in claim 1 wherein benzoyl peroxide comprises from about 0.1 to about weight percent of the second composition.

13. An apparatus as in claim 1 wherein the second composition is substantially anhydrous.

14. An apparatus as in claim 1 wherein the second composition comprises (i) a polar solvent; (ii) a thickening agent selected from the group consisting of acrylic acid polymers, polyacrylamides and combinations thereof; (iii) benzoyl peroxide; (iv) alkyl benzoate; and optionally (v) a synthetic cleanser.

15. A method of treating acne comprising simultaneously dispensing a first composition and a second composition, the first composition being substantially anhydrous and comprising i) a polar solvent; ii) an antibiotic; and iii) a thickening agent in an amount sufficient to impart to the first substantially anhydrous composition a viscosity of at least 1000 cenetipoise measured at room temperature, the thickening agent being selected from the group consisting of acrylic acid polymers, polyacrylamides and combinations thereof, the second composition comprising benzoyl peroxide; and contacting the first composition and second composition with the skin of a person afflicted with acne.

16. A method as in claim 15 wherein the first composition contains an antibiotic selected from the group consisting of erythromycin, clindamycin, tetracycline, derivatives of erythromycin, clindamycin, or tetracycline and pharmaceutically acceptable salts of erythromycin, clindamycin or tetracycline.

17. A method as in claim 15 wherein the second composition is substantially anhydrous.

18. A method as in claim 15 wherein the second composition comprises (i) a polar solvent; (ii) a thickening agent selected from the group consisting of acrylic acid polymers, polyacrylamides and combinations thereof; (iii) benzoyl peroxide; (iv) alkyl benzoate; and optionally (v) a synthetic cleanser.

19. An apparatus comprising:

a first chamber containing a first composition, the first composition being substantially anhydrous and comprising i) a polar solvent; ii) an antibiotic; and iii) a thickening agent in an amount sufficient to impart to the first composition a viscosity of at least 1000 cenetipoise measured at room temperature, the thickening agent being selected from the group consisting of acrylic acid polymers, polyacrylamides and combinations thereof;

a second chamber containing a second composition the second composition comprising i) a polar solvent; ii) a retinoid; and iii) a thickening agent in an amount sufficient to impart to the second composition a viscosity of at least 1000 cenetipoise measured at room temperature, the thickening agent being selected from the group consisting of acrylic acid polymers, polyacrylamides and combinations thereof; and one or more outlets for dispensing the first and second compositions.

20. An apparatus as in claim 19 wherein the first composition contains an antibiotic selected from the group consisting of erythromycin, clindamycin, tetracycline, derivatives of erythromycin, clindamycin, or tetracycline and pharmaceutically acceptable salts of erythromycin, clindamycin or tetracycline.

21. An apparatus as in claim 19 wherein the second composition comprises a retinoid selected from the group consisting of retinol, retinoic acid, retinyl palmitate, retinyl propionate, retinyl acetate and synthetic retinoid mimetics.

22. A method of treating acne comprising simultaneously dispensing a first composition and a second composition, the first composition being substantially anhydrous and comprising i) a polar solvent; ii) an antibiotic; and iii) a thickening agent in an amount sufficient to impart to the first substantially anhydrous composition a viscosity of at least 1000 cenetipoise measured at room temperature, the thickening agent being selected from the group consisting of acrylic acid polymers, polyacrylamides and combinations thereof, the second composition being substantially anhydrous and comprising i) a polar solvent; ii) a retinoid; and iii) a thickening agent in an amount sufficient to impart to the second composition a viscosity of at least 1000 cenetipoise measured at room temperature, the thickening agent being selected from the group consisting of acrylic acid polymers, polyacrylamides and combinations thereof; and contacting the first composition and second composition with the skin of a person afflicted with acne.

23. A method as in claim 1 wherein the first composition contains an antibiotic selected from the group consisting of erythromycin, clindamycin, tetracycline, derivatives of erythromycin, clindamycin, or tetracycline and pharmaceutically acceptable salts of erythromycin, clindamycin or tetracycline.

24. A method as in claim 22 wherein the second composition comprises a retinoid selected from the group consisting of retinol, retinoic acid, retinyl palmitate, retinyl propionate, retinyl acetate, and synthetic retinoid mimetics.

* * * * *